United States Patent [19]
Farin et al.

[11] Patent Number: 5,720,745
[45] Date of Patent: Feb. 24, 1998

[54] ELECTROSURGICAL UNIT AND METHOD FOR ACHIEVING COAGULATION OF BIOLOGICAL TISSUE

[75] Inventors: Günther Farin; Karl Ernst Grund, both of Tübingen; Klaus Fischer, Nagold-Emmingen, all of Germany

[73] Assignee: Erbe Electromedizin GmbH, Tubingen, Germany

[21] Appl. No.: 579,879

[22] Filed: Dec. 28, 1995

Related U.S. Application Data

[63] Continuation-in-part of Ser. No. 981,009, Nov. 24, 1992, abandoned.

[30] Foreign Application Priority Data

Sep. 26, 1995 [DE] Germany ............ 195 35 811.2
Oct. 18, 1995 [DE] Germany ............ 195 38 807.0

[51] Int. Cl.⁶ .................................................. A61B 17/36
[52] U.S. Cl. ........................ 606/49; 606/41; 606/40; 128/898
[58] Field of Search ............... 606/27–31, 40–42, 606/45–50; 128/898

[56] References Cited

U.S. PATENT DOCUMENTS

| | | | |
|---|---|---|---|
| Re. 33,925 | 5/1992 | Bales et al. ............... | 606/40 |
| 4,060,088 | 11/1977 | Morrison, Jr. et al. ....... | 606/49 |
| 4,753,223 | 6/1988 | Bremer . | |
| 4,781,175 | 11/1988 | McGreevy et al. . | |
| 4,901,719 | 2/1990 | Trenconsky et al. . | |
| 5,098,430 | 3/1992 | Fleenor . | |
| 5,122,138 | 6/1992 | Manwaring ............... | 606/46 |
| 5,195,968 | 3/1993 | Lundquist et al. ........... | 604/95 |
| 5,207,675 | 5/1993 | Canady .................. | 606/40 |
| 5,389,390 | 2/1995 | Kross . | |

FOREIGN PATENT DOCUMENTS

3710489  11/1987  Germany .

OTHER PUBLICATIONS

Grund et al., "Endoscopic Argon Plasma . . . Flexible Endoscopy" Endoscopic Surgery and Allied Technologies, No. 1, vol. 2, pp. 42–46, Feb. 1994.

Farin et al, "Technology of Argon Plasma . . . Endoscopic Applications" Endoscopic Surgery and Allied Technologies, No. 1, vol. 2, pp. 71–77, Feb. 1994.

"The Role Of Endoscopic Laser Therapy In Gastrointestinal Neoplasms" by Mark H. Mellow; pp. 17–21; Advanced Therapeutic Endoscopy.

Advanced Therapeutic Endoscopy; pp. 79–84; 1990; "Thermal Coagulation Therapy For Upper Gastrointestinal Bleeding".

"Techniques In Therapeutic Endoscopy", J.D. Waye MD, J.E. Greenen MD, D. Fleischer MD, Rama P. Venu MD, W.B. Saunders Co., Philadelphia, PA.

*Primary Examiner*—Michael Peffley
*Attorney, Agent, or Firm*—St.Onge Steward Johnston & Reens

[57] ABSTRACT

A method for coagulating tissue during endoscopic surgery by using argon plasma coagulation is described. An endoscope is used having a flexible, hollow tube inserted through one of the working channels of the endoscope. Inside the tube an electrode is arranged stationarily being offset from the exit opening at the distal end of the tube in such a manner that the electrode cannot come into contact with the tissue. Argon or another inert gas is supplied from a source of gas through the tube to the exit opening with such a low flow rate that gas exiting through the exit opening is a non laminar stream which forms an inert gas atmosphere between the distal end of the tube and the region of the tissue to be coagulated, while the exit is maintained at a distance from the tissue to be coagulated, whereby the area of tissue to be coagulated is positioned sidewardly of the extended longitudinal axis of the protruding end portion of the tube.

48 Claims, 14 Drawing Sheets

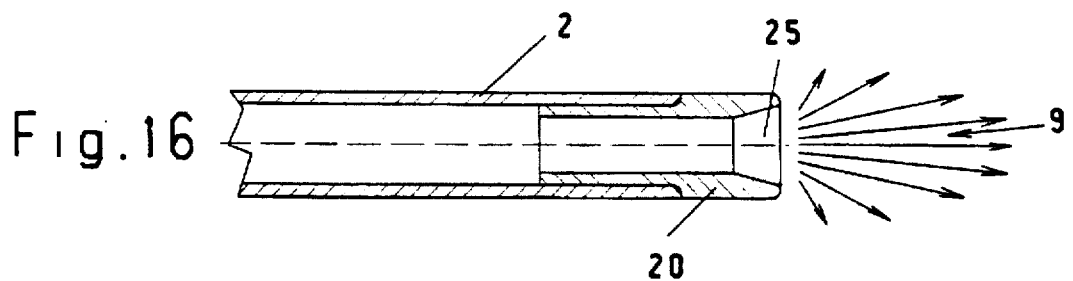
Fig.16
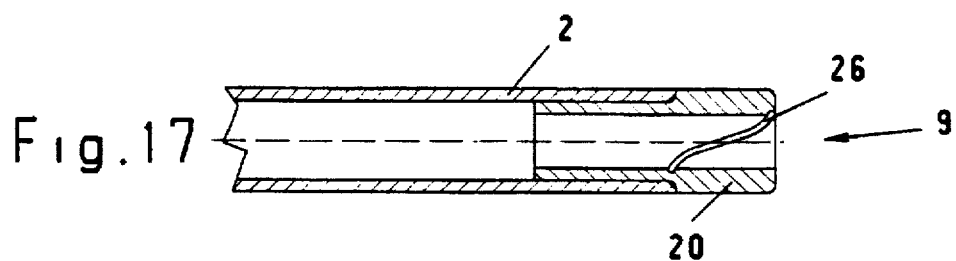
Fig.17
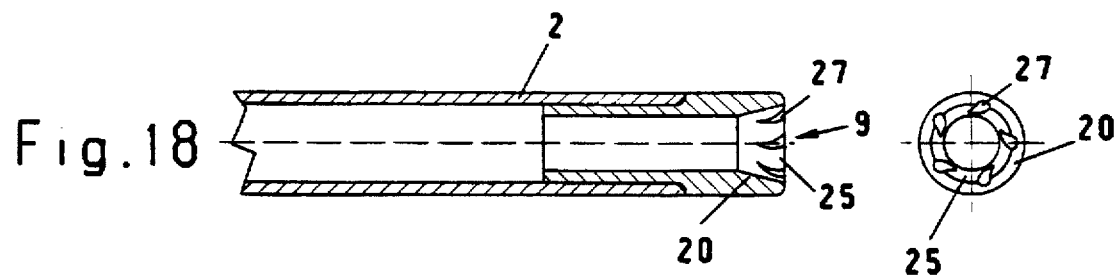
Fig.18
Fig.19

ELECTROSURGICAL UNIT AND METHOD FOR ACHIEVING COAGULATION OF BIOLOGICAL TISSUE

This is a continuation-in-part application of application Ser. No. 07/981,009 filed Nov. 24, 1992, (now abandoned).

FIELD OF THE INVENTION

The invention concerns a high-frequency electrosurgery device for coagulating biological tissue in the gastrointestinal tract, which device is mounted or is to be mounted on a surgical endoscope, having at least one working channel and a conduit for connection to a high-frequency voltage source for applying coagulation current to the tissue from the distal end of the endoscope.

BACKGROUND OF THE INVENTION

For stopping of bleeding by means of an endoscope in the upper as well as in the lower gastrointestinal tract several methods are known (compare "Advanced Therapeutic Endoscopy" Jamie Barkin-Cesar A. O'Phelan, Raven Press New York 1990 pages 17 to 21 and 79 to 84, and "Techniques in Therapeutic Endoscopy", Copyright 1987 by Gower Medical Publishing Ltd., New York, USA, chapters 1.7 to 1.15. Amongst such methods are thermal techniques for stopping bleeding which use the thermic coagulation effect and/or the effect of shrinking biological tissue because of exogenous and/or endogenous applied heat. In the case of exogenous application heat is conducted from a relatively hot probe, which is pressed against the source of bleeding to be stopped, by heat conduction into the tissue to be coagulated. In the case of the endogenous method e.g. high-frequency current is conducted through the tissue to be coagulated or a laser beam is radiated into the tissue to be coagulated, whereby the tissue is heated to the temperature necessary for coagulation.

In the exogenous methods by means of hot probes as well as in the endogenous methods by means of high frequency current the source of bleeding must be contacted with the probe or with the coagulation electrode, so that heat or electrical current can be conducted. A specific problem of such methods is therefore to be seen in the fact, that the eschar adheres to the probe or to the coagulation electrode, so that during removal of the probe or coagulation electrode the bleeding source is opened again. Another problem during coagulation by means of coagulation electrodes, which are brought into an electrically conductive contact with the tissue, is to be seen in the fact that the depth of the coagulation cannot be controlled in a satisfactory and sufficient manner. Therefore, the depth of the coagulation is dependent e.g. on the effective contact surface between the coagulation electrode and the tissue. Since thin walled tissue structures are present in said tract, the depth of the coagulation has to be considered. A specific risk in the case of coagulations by means of coagulation electrodes having relatively small surfaces or being thin or acute, which come into contact with the tissue is, that the coagulation electrode may cut into the tissue if the high-frequency voltage between the coagulation electrode and the tissue is higher than 200 Volts. Furthermore, such methods are rather time consuming, if large areas and diffuse bleedings shall be stopped. The stopping of bleeding by means of a laser beam requests rather expensive apparatus and instruments.

For the open surgery already equipment is known, by which an ionized inert gas like argon is conducted as a jet for creating an improved eschar in the stroma of tissue (U.S. Pat. No. 4,781,175=DE 37 10 489 A1). However, equipment of this type is not adapted for achieving coagulations in the said tract.

It is the object of the invention to provide for a device for an endoscopic coagulation, which avoids sticking of the coagulate at the coagulation electrode on the one hand, and to improve on the other hand the efficiency in the case of large area coagulations, whilst allowing control of the depth of the coagulation. It is another object to increase the diversity of the usability of an endoscope by an additional means, which can be assembled and disassembled, respectively, in a simple and fast manner, but nevertheless allowing reliable and safe operation of the coagulation device.

SUMMARY OF THE INVENTION

In accordance with the invention, an electrosurgical device for achieving coagulation of biological tissue preferably comprises an attachment or add-on piece, which can be attached to or removed from the end of a working channel of an endoscope, which attachment is having an orifice and in which attachment an electrode is arranged for supplying coagulation current and for ionizing a stream of inert gas exiting the distal end of said attachment. The electrode may be ring or pin shaped and is preferably fixed in such a distance from the plane of the face of the orifice, that during the endoscopic use the electrode cannot come into contact with the tissue. In this manner, it can be achieved that the coagulate or eschar does not stick to the coagulation electrode and that the coagulation gets out of control and therefore becomes too deep, so that thin walled organs could be perforated. In addition, a not intended cutting of the coagulation electrode into the tissue can be avoided in a reliable manner. If it is desired to provide a movable arrangement of the electrode, means are provided in order that the electrode can be safely arrested in a position, in which the distance from the plane of the face of the orifice is at least as long as a predetermined minimum distance, in order to avoid that the electrode comes into contact with the biological tissue.

The attachment is having such a length that the end of the attachment provided with the orifice can be seen well through a viewing lens at the distal end of the endoscope, which lens is associated with a viewing optics arranged in an instrument channel of the endoscope. Endoscopes available on the market may be used. The attachment can be provided on a rigid or flexible endoscope and consists preferably out of a flexible material, so that in the case of using a manipulator in a second working channel or in an instrument channel, which manipulator may be inserted from the distal or from the proximal end of the endoscope and is mechanically coupled with the attachment, in order to allow aligning of the orifice of the attachment or of a tube which can be inserted into the working channel from the proximal end thereof, whilst the attachment can only be inserted from the distal end thereof. In this manner the orifice provided at the attachment or at the tube can be aligned to the tissue to be coagulated, whilst the tissue to be coagulated can still be viewed through the endoscope. However, in many cases it is not necessary to provide a manipulator of the mentioned type, as will be described in connection with the various embodiments of the invention. Since the working channel itself serves for the delivery of gas and since the distal end of the attachment necessarily comes into the field of view of the viewing lens, a rather simple and reliable attachment of the device is possible by auxiliary personnel even during an operation.

In accordance with another embodiment of the invention a tube out of electrically not conducting material is arranged in a movable manner in the working channel, which tube is preferably a flexible hose, so that in the case of a rigid and also in the case of a flexible endoscope a desired alignment of the distal end of the hose or a tilting of the end of the hose can be performed, e.g. by providing an articulated joint near to the distal end of the hose.

Instead of a ring shaped electrode fixed at the inner wall of the attachment or of the tube a metallic pin may be provided along the axis of the attachment or the tube. The opening of the orifice may be aligned in the axial direction or may form an angle with the axial direction. The orifice may also be aligned in a radial direction and several orifices can be provided along the circumference of the attachment or the tube.

At the distal end of the respective attachment or tube spacer means are preferably provided, in order to provide for a proper distance between the opening of the orifice and the region to be coagulated. The spacer means may be a finger-type or a disk-type spacer.

Specific advantages of the invention can be seen in the fact, that a large variety of endoscopic operations can be performed, e.g. stopping of bleeding by coagulation, desiccation of the surface, eradication of rests after a polypectomic operation, forming eschars on tumors or thermic tissue marking.

The invention and its particular features and advantages will become more apparent from the following detailed description considered with reference to the accompanying drawings.

BRIEF DESCRIPTION OF THE DRAWINGS

FIGS. 16 to 19 and 21 are schematic sectional views of preferred exit openings of tubes to be inserted into a working channel of endoscopes of FIG. 1.

DETAILED DESCRIPTION OF THE INVENTION

Figure 1:
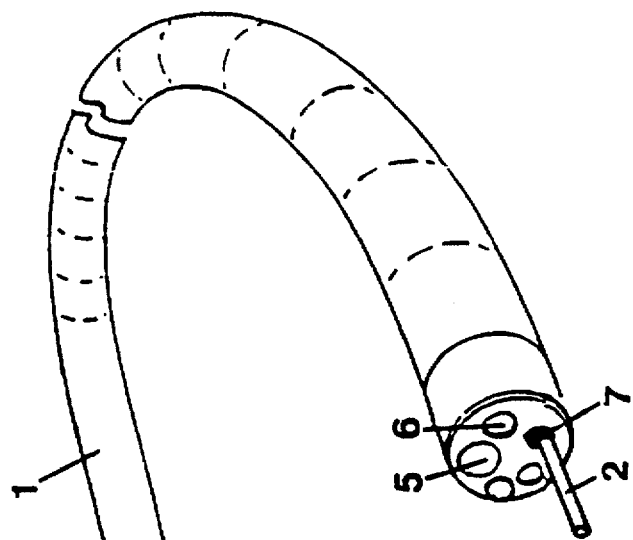
FIG. 1 is a partially schematic view of a flexible endoscope with a device in accordance with the invention.
Figure 1:
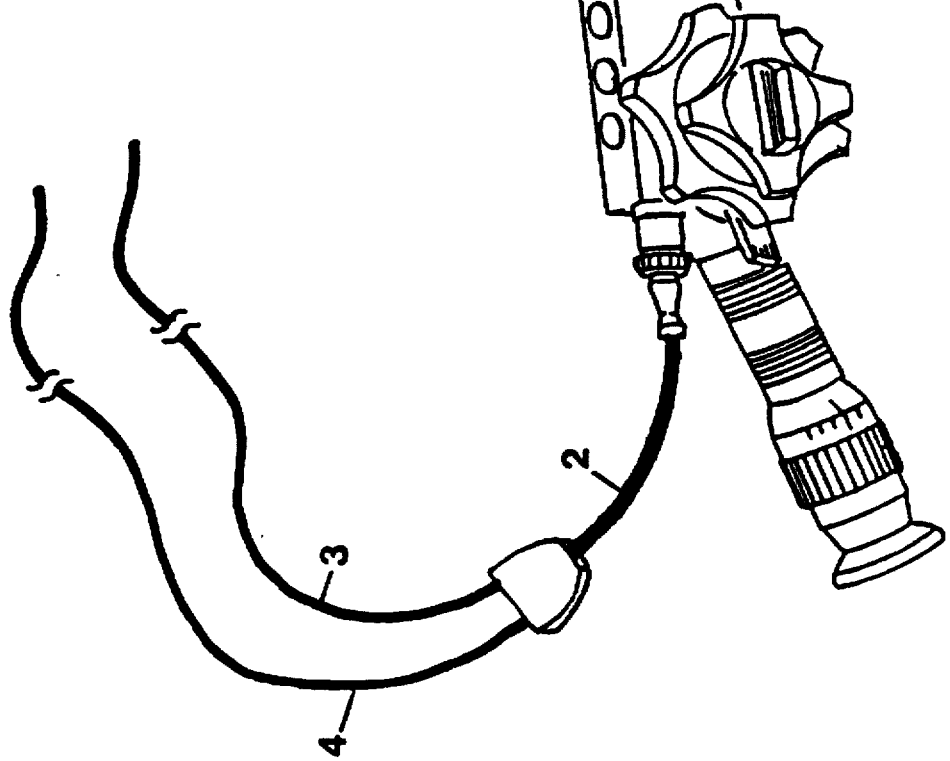

FIG. 1 shows a flexible endoscope known as such, which is provided with a device in accordance with the invention, which device comprises a tube out of PTFE or the like material. The endoscope will be described below in a more detailed manner in connection with FIGS. 2 to 4. The tube 2 protrudes out of the distal end of a working channel 7. At the distal end of the endoscope a lens 5 of a viewing optics is provided. Furthermore, the distal end of a second working channel 6 can be seen. The tube 2 is connected through a gas supply conduit 3 with a not shown gas reservoir which may be a gas cylinder filled with argon. A connection circuit 4 serves for a connection to a not shown high-frequency voltage source for applying coagulation current to the tissue from the distal end of the endoscope, from which an endpiece of the tube 2 is protruding.

Figure 2:
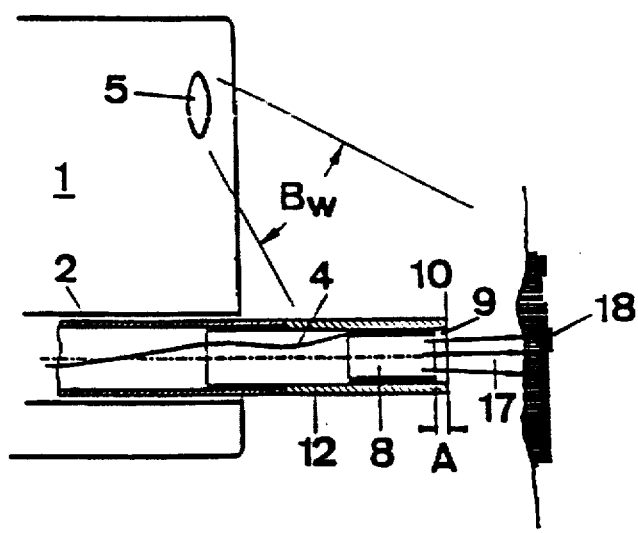
FIGS. 2 to 12 are schematic sectional views of various different distal ends of endoscopes of FIG. 1.
Figure 3:
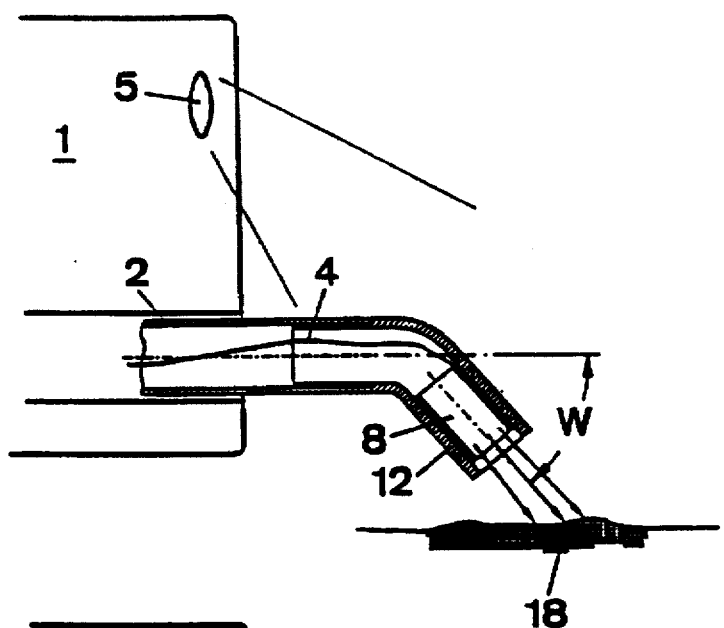
Figure 4:
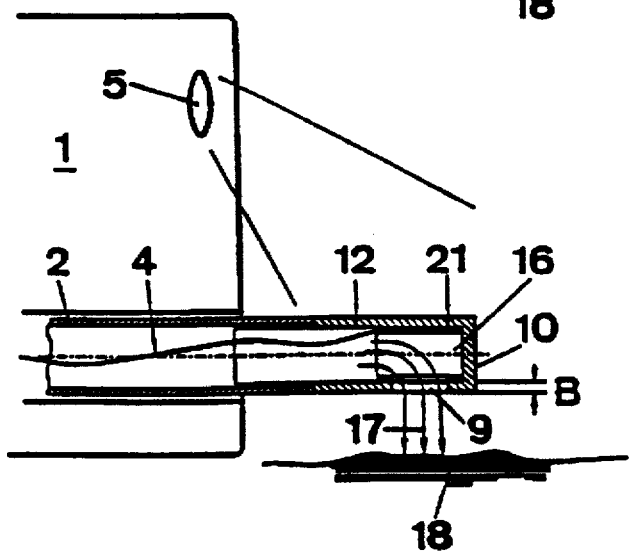

FIGS. 2 to 4 show three different embodiments of the tube 2 in FIG. 1. In all three embodiments the tube 2 consists out of flexible material. It is advantageous and important, that the tube 2 may protrude so far out of the distal end of the endoscope 1, that the opening 9 of the orifice 16 is aligned or may be aligned in such a manner, that the gas stream 17 is directed onto the tissue 18 to be coagulated. In FIG. 2 the tissue 18 to be coagulated is in the axial direction of the distal end of the endoscope 1, so that the opening 9 of the orifice 16 should also be aligned in axial direction. In FIG. 3 the tissue 18 to be coagulated is not in the axial direction of the distal end of the endoscope I and the tube 2. Therefore, the distal end of the tube 2 is angled with an angle W. FIG. 4 shows another embodiment, in which the tissue 18 to be coagulated is parallel to the axial direction of the distal end of the endoscope 1, so that the opening 9 of the orifice 16 is oriented in radial direction. Whilst the tube 2 may be inserted in the embodiments shown in FIGS. 2 and 4 from the proximal to the distal end through the endoscope, in the embodiment as shown in FIG. 3 the device is inserted from the distal end to the proximal end through the endoscope. In FIGS. 2 to 4 the electrode 8, 21 is fixed at the distal end of the tube 2, which electrode serves for ionizing the gas. This electrode 8, 21 is connected through a connection line 4 with the not shown high-frequency generator, e.g. with a high-frequency electrosurgical apparatus. In the embodiment in FIG. 4 the face 10 of the endpiece 12 is closed and the gas 17 exits radially out of the orifice 9 of nozzle 16. The electrode 8 is arranged in all embodiments in such a manner, that substantially no direct contact is possible with the tissue to be coagulated or with other tissue, out of which reason the electrode 8 is offset from the face 10 of the tube 2 and the endpiece 12, respectively, for a minimum distance A, which distance may be about 1 mm/kV. The end portion 12 consists out of temperature resistant material like PTFE or ceramics. The tube 2 may have an outer diameter of e.g. about 2.5 mm and may consist out of PTFE or the like material having similar properties. In all embodiments as shown in FIGS. 2 to 4 the distal end of the device can be arranged in the angle of view Bw of the lens 5 of endoscope 1.

Figure 5:
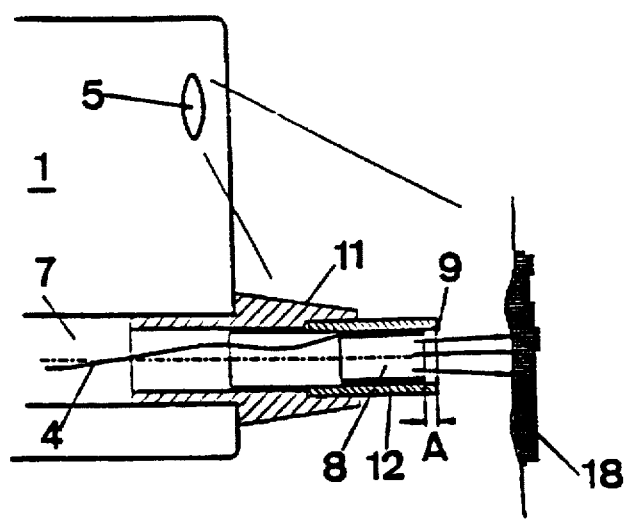
Figure 6:
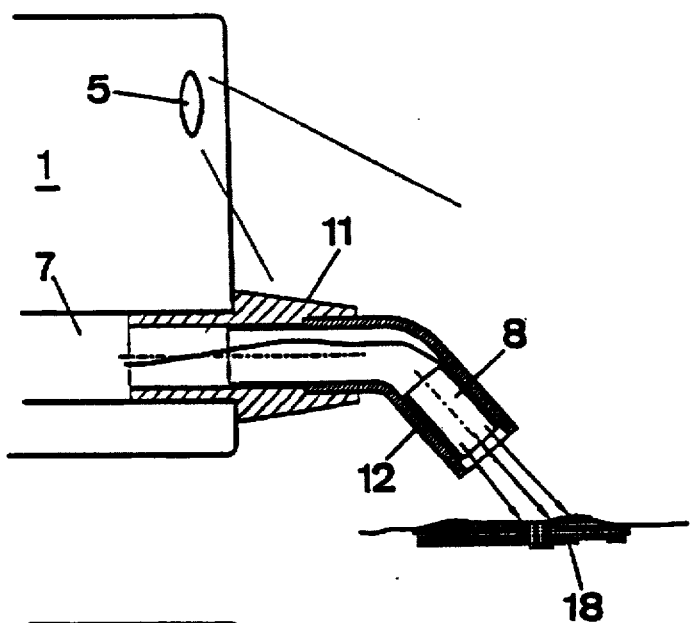
Figure 7:
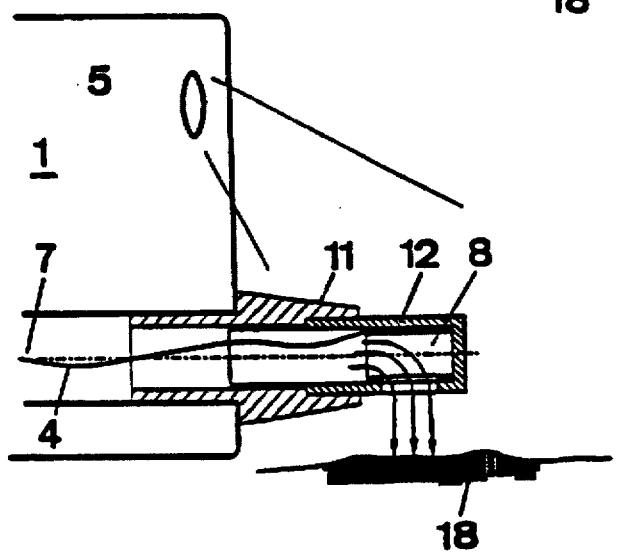

FIGS. 5 to 7 show embodiments of the invention, in which attachments 11 are inserted into the distal end of the working channel 7 of the endoscope 1, and in which the working channel 7 serves as gas supply conduit 11. Also in these embodiments like in FIGS. 2 to 4 the end pieces 12 are made out of temperature resistant material like PTFE or ceramics, in which end pieces the electrode 8 is fixed, which electrode is connected through the connection line 4 with the not shown high-frequency generator. In all embodiments shown in FIGS. 5 to 7 the distal end of the device can be arranged in the view angle Bw of the viewing optics of the endoscope 1.

Figure 8:
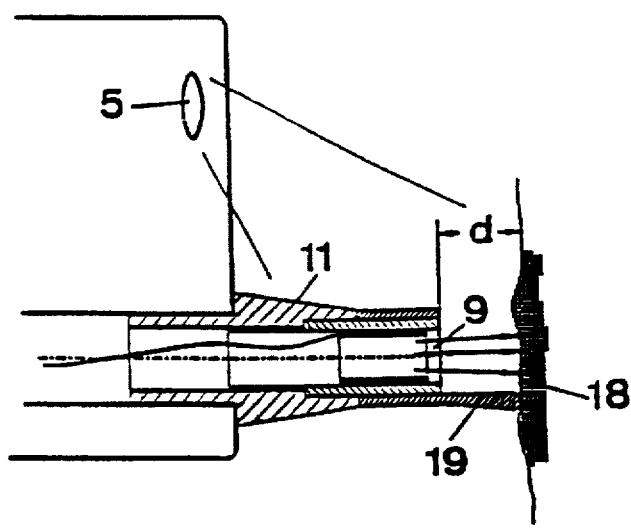
Figure 9:
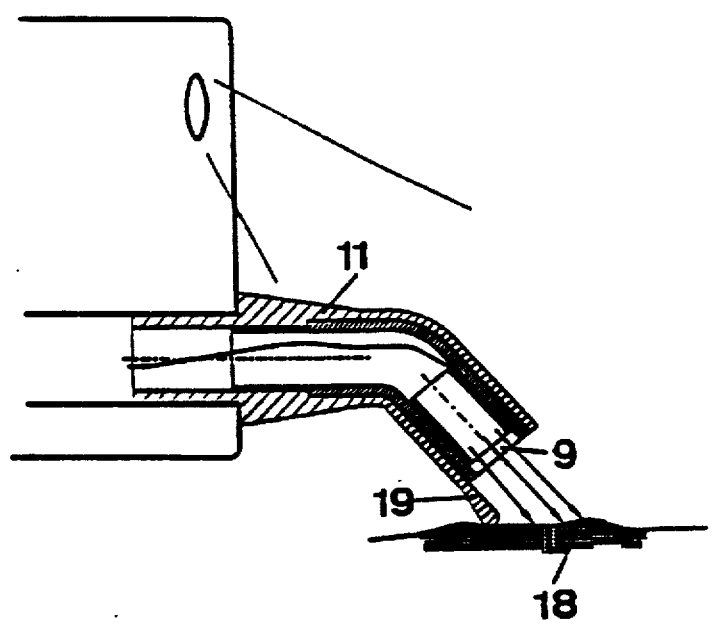
Figure 10:
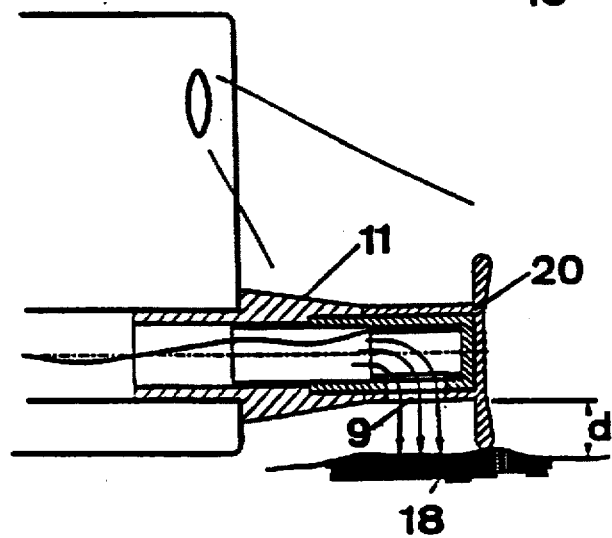

In the embodiments as shown in FIGS. 8 and 9 spacer means are provided in the form of a spacer finger 19 protruding from the face 10 of the orifice 9. In the embodiment in FIG. 10 at the distal end of the tube 2 or the attachment 11, respectively, a round disk 20 is provided as distance means, in order to provide for a minimum distance d between the orifice 9 and the tissue to be coagulated, which distance d is determined in FIGS. 8 and 9 by the respective distance finger.

Figure 11:
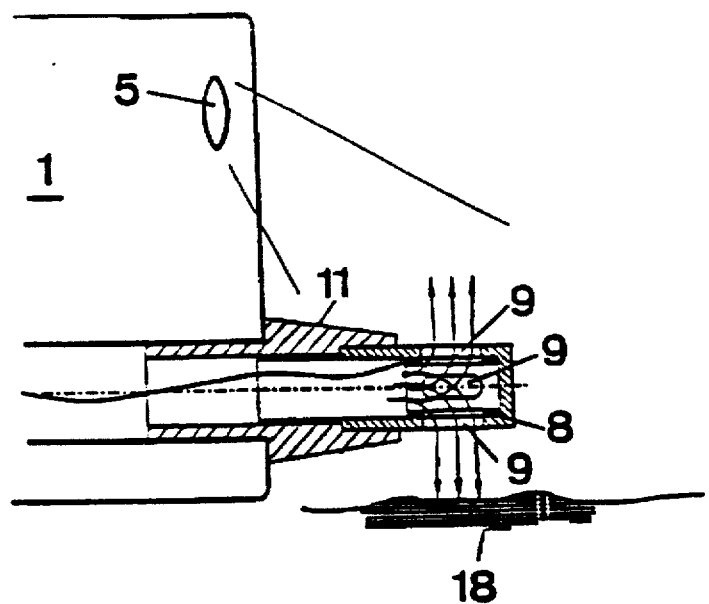

In the embodiment shown in FIG. 11 several orifices 9 are provided along the circumference of the attachment 11 or the tube 2, respectively, which are arranged in the region of the electrode 8 and are aligned in radial directions. The use of several radially aligned orifices has the purpose, that the gas may flow into different directions, whereby ionizing in each case takes place at the orifice, the distance of which between electrode 8 and tissue 18 is smallest. A specific advantage of this embodiment with several orifices is to be seen in the fact, that the person using the endoscope needs not to manually align the orifice 9 with the tissue 18 to be coagulated, as shown in the embodiments in FIGS. 7 and 10, but has only to move the distal end of the endoscope into the region of the tissue to be coagulated, so that ionizing automatically takes place always on the side, where the distance between tissue 18 and electrode 8 is shortest.

Figure 12:
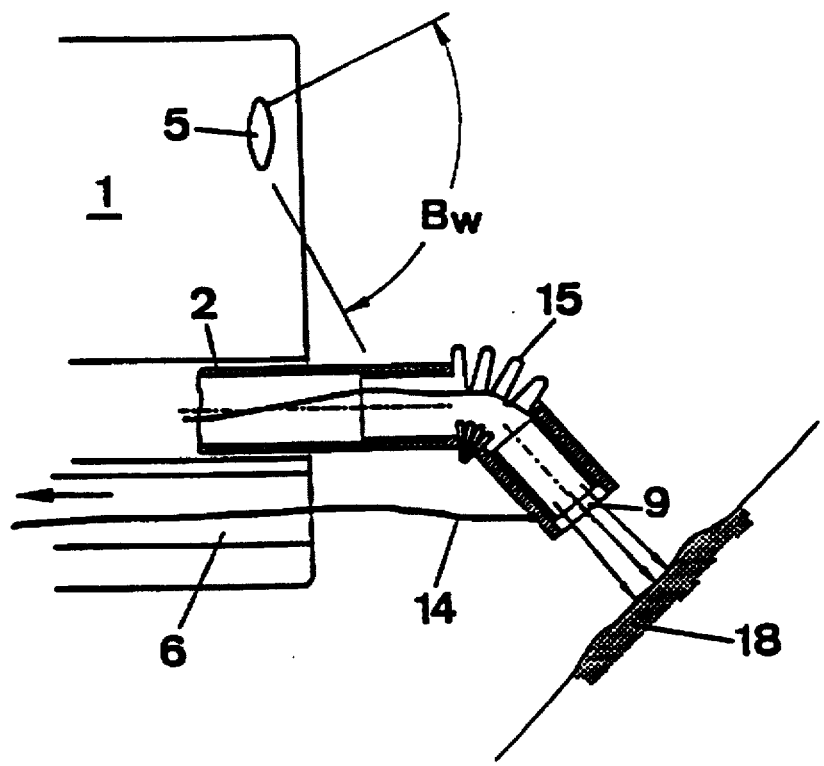

In the embodiment shown in FIG. 12 the distal end of the tube 2 or of the attachment 11, respectively, may be tilted with respect to the exit direction, e.g. by providing flexible bellows 15 between the tube 2 and the orifice 9, whereby the adjustment of the direction takes place by means of a manipulator 14, which simply may be rope 14, which rope extends through the second working channel 6 of the endoscope, so that the direction of the orifice 9 can be changed by pulling the rope at the end of the endoscope in the direction of the arrow. In the rest position the direction of the orifice 9 may be aligned in the axial direction. Instead of the rope 14 also a rod or a sufficiently rigid wire or pin may be used, which preferably is made out of non-conductive material, so that an adjustment could not only be made in the direction of the shown arrow, but also in the opposite direction.

Figure 13:
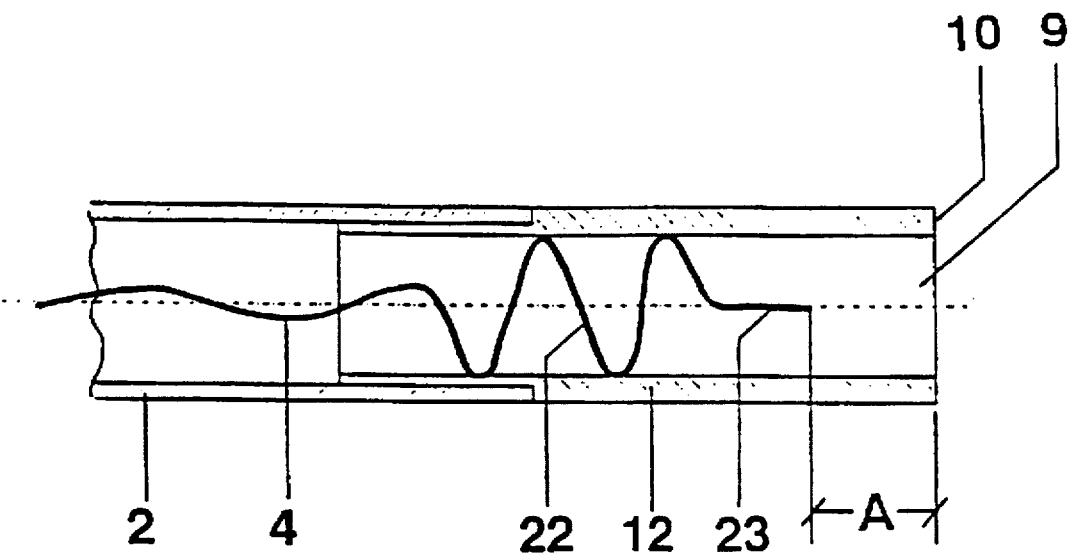
FIGS. 13 to 15 are schematic sectional views of different end portions of tubes to be inserted into a working channel of endoscopes of FIG. 1, showing the attachment of a pin-type electrode.
Figure 14:
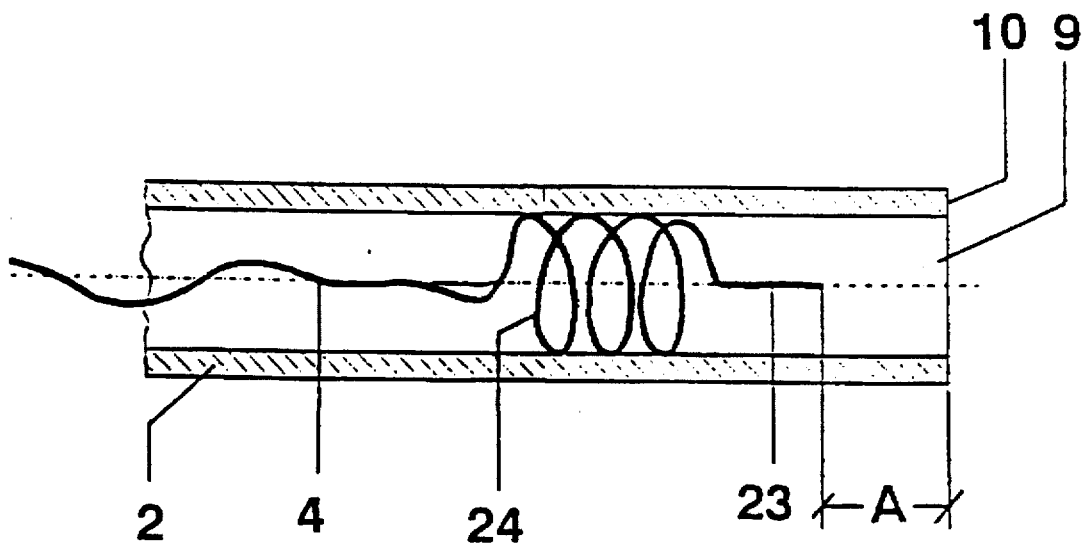

FIGS. 13 and 14 show embodiments for permanently fixing an electrode 23 in a defined distance A from the distal end 10 (FIG. 2) of the tube 2 or of a temperature resistant extension 12 of the tube 2 of the orifice means 9. In FIG. 13 a pin-shaped electrode 23 extends from a wave-like or undulated formed spring wire, whereby the wave-type portion 22 presses against the surface of the inner wall of the tube and therefore cannot be shifted from the proximal to the distal end. The wave-like shaped portion of the spring wire may also directly serve as an electrode. In FIG. 14 the electrode is permanently fixed in such a manner, that the electrode 23 extends from a spiral-shaped portion 24 of wire 4 pressing against the inner wall of the tube 2 and therefore cannot be shifted from the proximal to the distal end, so that the safety distance A is maintained. The spiral-shaped portion of the spring wire may also directly serve as an electrode.

Figure 15:
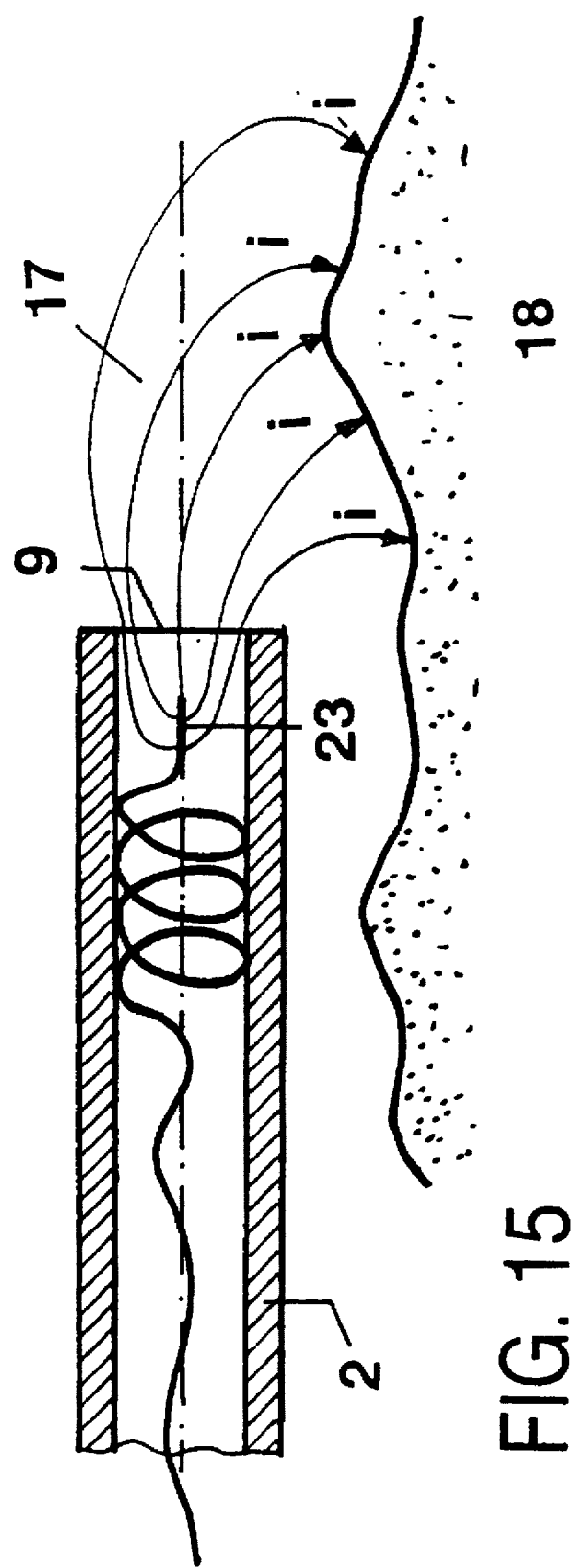

In many cases it is not necessary to direct the axis of the orifice 9 of the tube 2 or the attachment 11 to the surface to be coagulated, as shown in FIG. 15, since the ionization of the gas stream 17 is normally automatically directed to the adjacent surface of tissue 18, even if the tissue 18 is in a position as shown in FIGS. 3, 4, 6, 7 and 9 to 12, whilst the axis of the tube 2 or the attachment 11 is oriented as shown in FIGS. 2, 5 and 8.

However, the orifice 9 in combination with a manipulator is of advantage in such cases, in which the view angle Bw is large, e.g. larger than 90°. The angle of view means the image angle under which the complete image may be seen. As in the case of wide angle lenses of cameras, e.g. an angle of view up to 180° is possible, whilst in the case of telelenses only an angle of view of about 20° is possible. In the case of different endoscopes the angle of view of the respective endoscope may be e.g. 30° only, so that in the case of relatively small movements the image field of interest cannot be seen any more. Therefore, it is desirable to use an endoscope with such a large angle of view, that the endoscope needs not to be moved, but the orifice can be moved by the manipulator within relatively large regions, whereby the image of interest remains visible. Therefore, the endoscope is not moved in the direction of interest, but the orifice is moved by means of the manipulator.

FIGS. 16 to 19 show different and presently preferred embodiments of the exit openings 9 at the distal end of tube 2. The structure of the distal end in such embodiments is in contrast to the structure of the nozzle as shown in the McGreevy patent (U.S. Pat. No. 4,781,175) in FIGS. 4 to 6, since the structure of the distal end region of the known hand piece to be used in open surgery is characterized by a funnel-like configuration 140, from which the gases flow into the nozzle 52. The funnel-like configuration 140 and the length and diameter relationship of the nozzle 52 cause the gases to exit the nozzle 52 in a substantially directed or laminar stream or jet (column 10, lines 28 to 32). In order to achieve the laminar and directed jet the preferred flow rates are between about 4 l/min and 13 l/min. The main idea described in this reference is to be seen in the fact, that a laminar jet can be directed to the tissue to be coagulated in such a manner, that the flow rate is sufficient to clear natural fluids from the tissue and to substantially expose the tissue stroma. However, this means that the gas jet always has to be directed exactly to the place, where tissue to be coagulated is present. A further substantial problem in the case of this known arrangement is also to be seen in the fact, that the necessarily high gas flow rate may cause the result, that gas enters into open blood vessels, which in the case e.g. of the use of argon may cause damages of the patient, under certain conditions even lethal damages. A further problem in the case of such a device may be seen in the fact, that during an endoscopic operation the gas jet cannot be exactly directed to the surfaces to be coagulated because of the limited possibilities to move the exit opening to desired positions.

Figure 20:
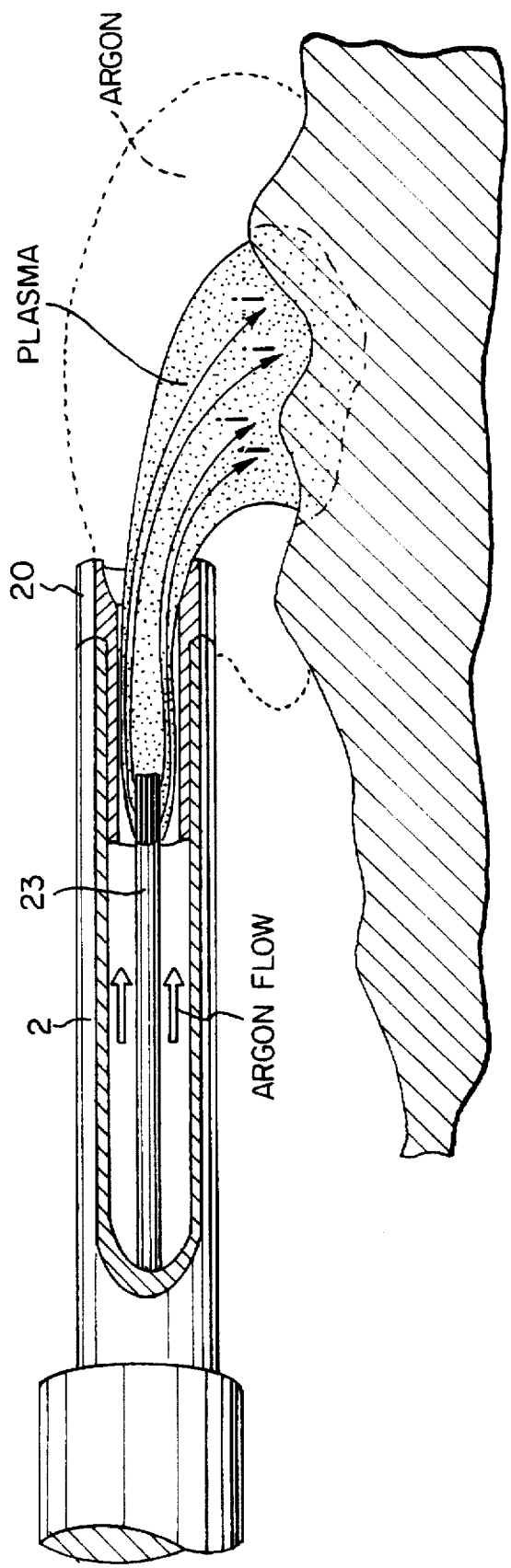
FIG. 20 is a schematic view of a distal end of the endoscope of FIG. 1 showing how an argon cloud fills the area to be coagulated with performing substantial mechanical action to fluid at the tissue.

In the case of the embodiment of the invention as shown in FIG. 16 an end piece 20' out of a temperature resistant material like ceramics is inserted into a distal end portion of tube 2. If a ceramic endpiece 20 is used, sterilization is possible to allow repeated use. If such an end piece 20 is not used, tube 2 could be sold as a disposable article in a sterile wrap. The end piece 20 out of ceramics has an outwardly diverging end portion 25 adjacent the exit opening 9. The jet out of ionizable gas like argon or helium is not guided in such a manner, that it is practically always guaranteed, that the flow rate is sufficient to clear natural fluids from the tissue. If in the case of the invention strong bleeding takes place, the flow rate of the gas should not be increased to a flow rate sufficient to clear natural fluids because of the danger of an embolism. If strong bleeding occurs other known possibilities should be used to close blood vessels. In the case of the invention which allows endoscopic use in the gastrointestinal tract, rather low flow rates of e.g. about 1 l/min or even lower flow rates are sufficient, in order that the rather small space between the electrode 8 (FIG. 2) or electrode 23 (FIG. 15), respectively, and the tissue 18 to be coagulated is completely filled by an argon cloud as shown in FIG. 20 and in order to remove air, but not in order to perform a substantial mechanical action to fluid at the tissue. Therefore, the supplied gas will not penetrate into open blood vessels. Whilst in the case of a laminar gas jet only the region between the place at which the gas jet impinges upon the tissue and the electrode is substantially free of environmental air, in the space surrounding the gas jet a rather vigorous air stream is caused because of the suction function of the laminar gas jet (similar like in the case of a steam-jet pump), so that in the surrounding space only a low concentration of ionizable gas is present. By the gas supply as performed by the invention a function to the contrary is achieved. The space between the exit opening 9 of the gas and the tissue 18 to be coagulated in the relative positions of the axis of the tube 2 and the surface of the tissue 18 to be coagulated as shown in FIG. 15 and FIG. 20 is filled with the ionizable gas, so that a discharge "around the corner" takes place, which means in other words, that in the case of the invention the current i from the electrode can flow to the regions of the tissue having the lowest resistance. Such regions are simultaneously the regions to be coagulated. This also means, that the surgeon needs not take exactly aim to such places, in which tissue to be coagulated must be visible in order to be hit. Thereby endoscopic operations are substantially simplified in regions which are not easily accessible. It also means that the duration of the operation can be shortened.

Preferably, the means for conducting the gas stream are arranged to allow that the ionizable gas displaces steam issuing from the heated tissue regions slowly, but is not blown away abruptly. This causes a rather gentle performance of the coagulation. In the case of a sufficient low energy supply an electrically isolating layer out of steam is formed against the ionized argon or the like inert gas. Therefore in this tissue region no coagulation current can enter any more and the further heating of the tissue is interrupted. If the ionizable inert gas displaces the steam, the coagulation current begins to flow again, so that a further heating of the tissue takes place. Therefor, a substantially self-regulating procedure is performed, avoiding that the tissue is torn in the case of too rapid heating, which may happen under certain conditions if the steam cannot issue sufficiently rapid.

Preferably adjustable flow means or regulating means are provided, in order that a predetermined gas flow rate can be adjusted and in order that the conditions can be optimized to achieve the above mentioned advantages.

The means for conducting the gas comprise in the case of an embodiment of the invention at least one diffusor, namely a diverging end portion 25, by which it can be achieved, that not a laminar gas jet is formed, but a "cloud" out of gas exiting from the exit opening 9. Furthermore, turbulences may be caused by using turbulence devices, which produce swirl within the gas stream. Thereby it is further guaranteed, that no laminar gas stream is produced and that the space between the electrode and the surface of the tissue is filled with the inert gas, without that gas (air is sucked from the environment.

Figure 1A:
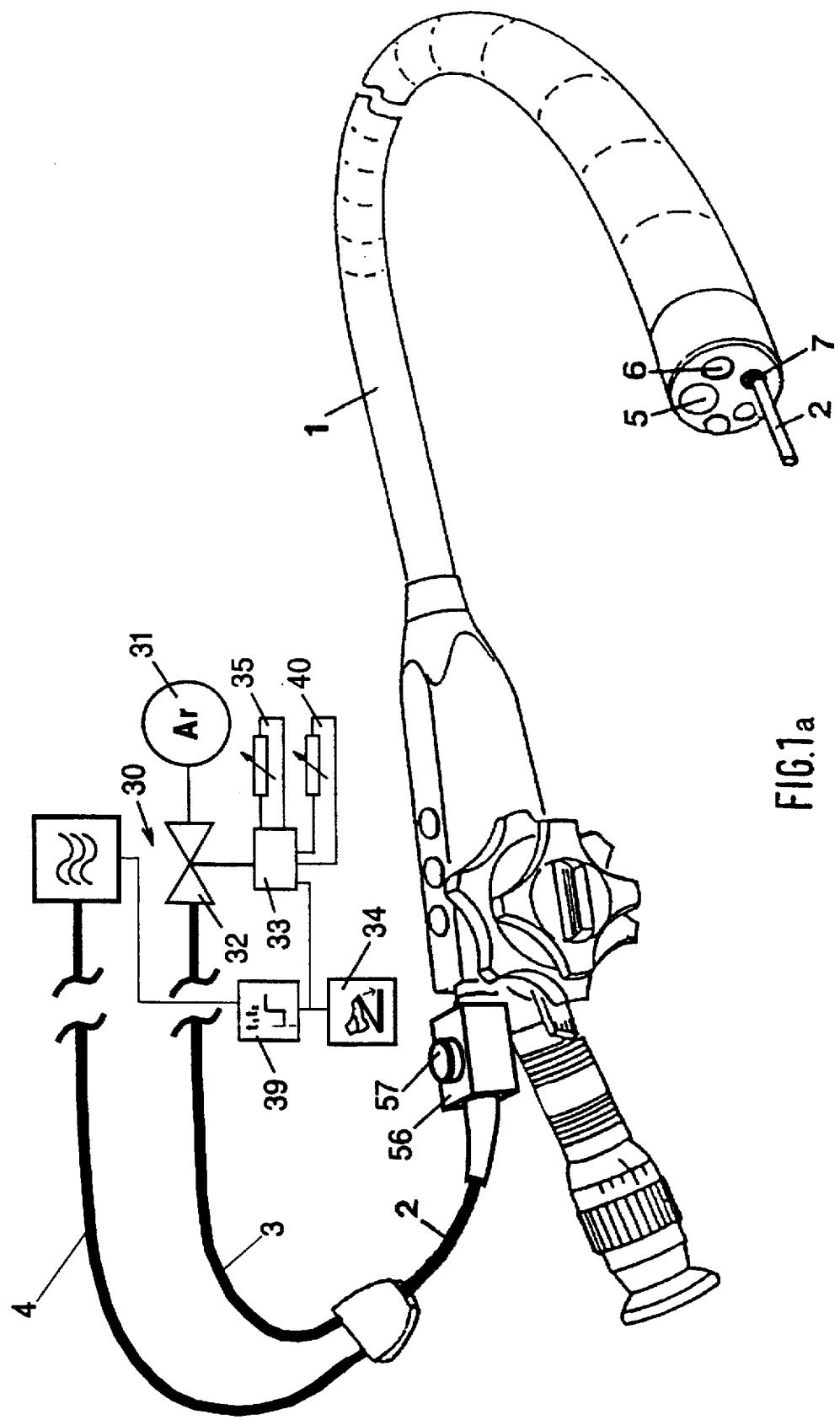
FIG. 1a is a partially schematic view of a preferred embodiment and preferred assoc. apparatus of a flexible endoscope of FIG. 1.

A preferred field of use of a diffusor in accordance with the invention is endoscopic use. For the endoscope as shown and described in connection with FIG. 1 gas supply and control means 30 may be used, as shown in FIG. 1a.

The proximal end of the tube 2 is connected with the gas supply conduit 3 to a valve 32 and an argon reservoir 31, which is preferably a pressurized gas cylinder filled with argon. The valve 32 is adjusted by means of a regulating assembly in accordance with the output signal of a regulator 33, which signal depends on the output signal of a measuring organ and the difference of which to a nominal value from a nominal value adjuster 35 is formed. The measuring organ measures preferably the mass- or volume stream of gas, which flows through valve 32. This assembly for supplying argon (or another ionizable inert gas) is provided with reference numeral 30.

Together with the adjuster 35 a second nominal adjuster 40 can be used in order to avoid the following problem. If the adjuster flow rate of the regulated gas stream is very low, it may happen that because of overpressure in a body cavity or because of capillary forces fluid may enter into the tube. Therefore, in the embodiment as shown in FIG. 1a a first adjuster 35 and a second adjuster 40 are provided, which provide a first flow rate during standby, but a second flow rate during activation. Thereby it can be avoided that blood rests accumulate in the tube which may cause during a later operation at another patient the danger of infection, e.g. hepatitis infections and HIV-infections. In order to avoid danger of infections it is also possible to flow sterile liquid through the tube, in order to avoid the danger of infections. Actuation of a foot switch 34 allows to actuate the gas valve 32 and the generator HF for the high frequency energy. Between foot switch 34 and the generator HF a delay circuit 39 is connected, since it is important that at first the inert gas is sufficiently supplied whilst the generator is only actuated after a sufficiently long delay time after a sufficient supply of inert gas.

FIG. 16 shows the distal end of the tube 2 in FIG. 1, into which a ceramic end piece 20 is inserted. In this embodiment of the invention the exit opening 9 is shaped as a diffusor 25 in the form of a cone-shaped or outwardly diverging end portion 25. This diffusor 25 does not produce a laminar gas stream, but a diverging gas stream being slightly swirled in the border zones. Therefore, also in the border zones of the argon gas cloud shown in FIG. 20 a high concentration of the argon gas is present. Therefore, in spite of or just because of the relatively low gas velocity of the inert gas a gas cloud is produced between the electrode 8 in the previously described embodiments and the tissue so that a discharge can take place. The plasma jet 17 produced thereby corresponds to the electric field lines as shown in FIG. 15 and FIG. 20, which plasma jet is always travelling to the places with the lowest resistance in the tissue, therefore to the places which are (still) wet, so that a "self-active" search for tissue to be coagulated takes place. Simultaneously to this locally self-regulating procedure also a time-regulation takes place, since the steam issuing out of the treated tissue regions displaces the inert gas and forms therewith an insulating not ionized layer. Therefore in such regions no (further) discharge or heating, respectively, takes place. After a certain time period the steam condenses or is displaced by the inert gas slowly, so that a discharge may be "reignited" also in this region, until the tissue is coagulated in such a manner, that a discharge can not take place any more, or the operator interrupts the operation, respectively. By this timely self-active regulation it is guaranteed, that a too rapid vaporizing of the water in the tissue normally would not take place, which might cause tearing of upper tissue layers. The coagulated tissue zones are therefore gently treated with the device in accordance with the invention, so that a good eschar can be obtained.

In the embodiment as shown in FIG. 17 a cylindrical end piece 20 with a helical notch 26 is shaped in such a manner, that the exiting gas jet is provided with a spin, which (like a conical exit opening) hinders producing of a too sharp laminar gas jet.

In the embodiment shown in FIG. 18 the end piece 20 does not only have a conical or diverging end portion 25, but in the surface of the diffusor 25 additionally a number of notches 27 in a configuration shown in FIGS. 18 and 19 are formed, which notches cause swirling in the border zones and also additionally produce spin.

Whilst the flow-rate scale for gas volume flow on the argon gas valve used in connection with equipment for the open surgery normally indicates flow rates between e.g. 1 to 10 l/min, the actual flow rate is much smaller in the case of the described use in combination with an endoscope, since such scales usually presuppose a negligible flow resistance of the applicator and its connection line. Gas volume flow (V) is a function of the pressure (P) and the internal flow resistance ($R_i$) of the gas source as well as of the flow resistance ($R_a$) of the applicator including its connecting lines:

$$V=f(P/R_i+R_a).$$

In a practical embodiment the tube had an inner diameter of 0.8 mm and the actual flow rate during an above described coagulation was 0.2 l/min. However, depending on desired conditions, somewhat higher or even lower diameters and flow rates may be adjusted, and two adjusters 35, 40 as shown in FIG. 1a may be adjusted to different flow rates.

Figure 21:
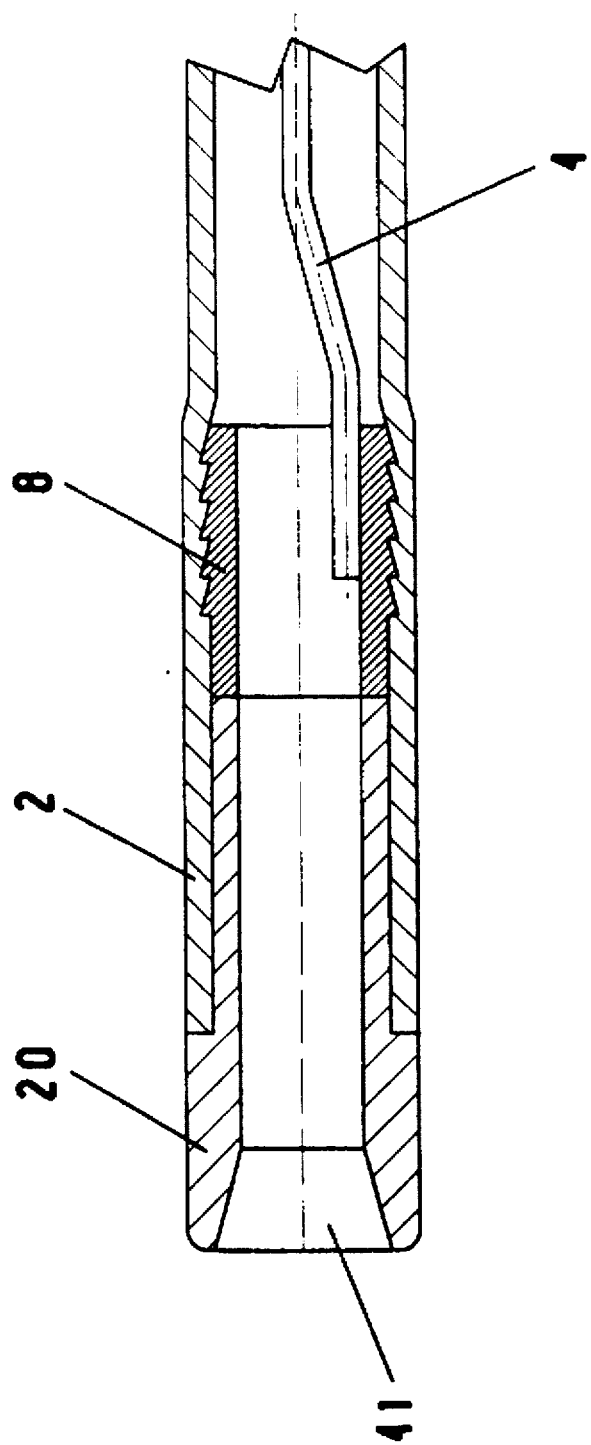

A presently preferred distal end portion of tube 2 with the end piece 20 out of ceramics inserted therein is shown in FIG. 21, where a hollow cylindrical electrode 8 is arranged connected with a connection line 4 for connecting with the high frequency voltage source for supplying coagulation current to the tissue from the distal end of the endoscope. Also in this case rather large areas of tissue can be coagulated sidewardly from the axis 41 of tube 2 as shown in FIGS. 15 and 20, in which cases pin type electrodes 23 are provided.

Figure 22:
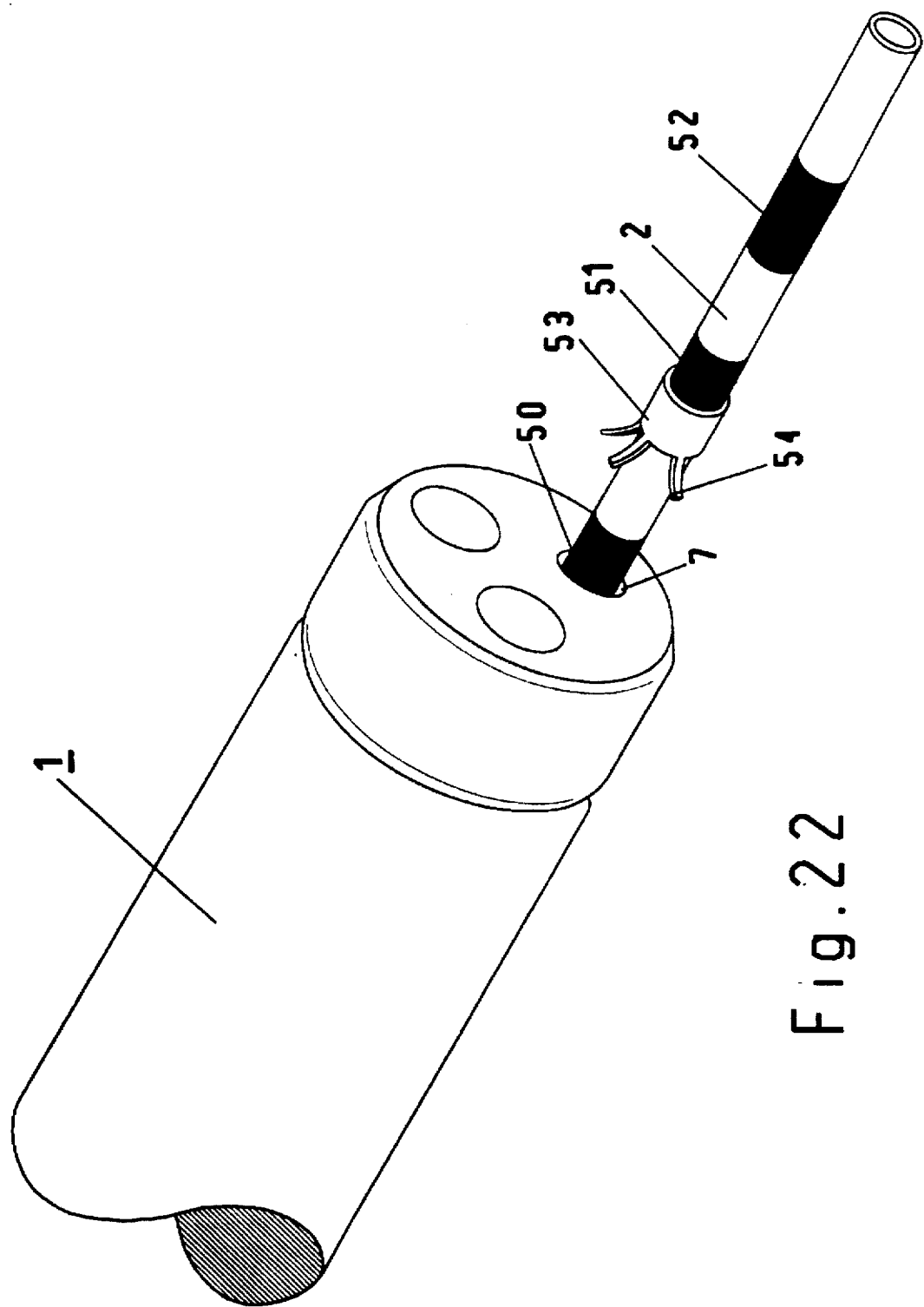
FIGS. 22 to 23 are schematic views of barbs of tubes to prevent unintended retraction of the tube into the endoscope of FIG. 1.
Figure 23:
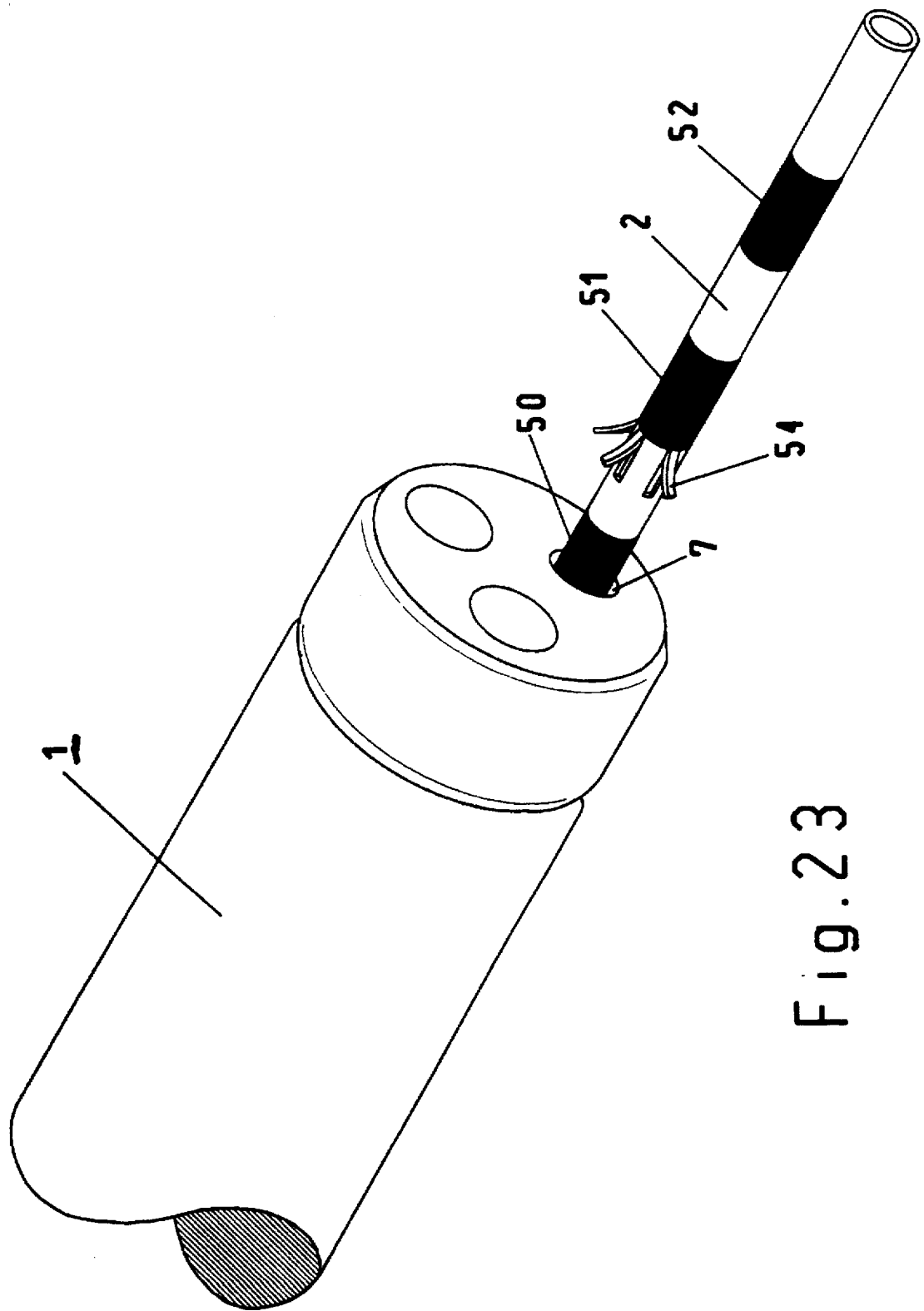

As may be seen from FIGS. 22 and 23, the distal end portion of tube 2 protruding from the end of the working channel 7 of the endoscope 1 may be provided with markings 50, 51, 52. An arrangement of such ring shaped markings allows to observe, how far tube 2 protrudes out of the distal end of the working channel 7 of the endoscope. On the monitor often only a distorted display of the tube can be seen, so that it is not possible without the mentioned ring shaped markings 50, 51, 52 to recognize how far the tube 2 protrudes out of the distal end face of the endoscope 1. Since high voltages are applied to the electrodes 8 or 23, respectively, electrical discharges to the distal end of the endoscope could occur, if the tube 2 is not protruding along a sufficient length out of the distal end face of the endoscope 1, whereby damages at the endoscope may be caused.

As may be seen from FIG. 22, a not intended retraction of tube 2 into working channel 7 can be avoided, if a sleeve 53 is fixed at the outer circumference of tube 2, which sleeve is provided with barbs 54 allowing to move the tube 2 in the distal direction to protrude for a desired length out of the working channel 7 if a sufficient force is exerted by the surgeon, whilst the surgeon cannot retract the tube 2 into the working channel 7, as soon as the barbs 54 come into engagement with the distal end face of the endoscope 1. Therefore, the surgeon recognizes because of the frictional forces to be overcome during advancing the tube out of the working channel, that the barbs 54 are not in engagement any more with the working channel, since tube 2 is protruding sufficiently. On the other hand, the surgeon can not retract the tube any more into the working channel 7 inadvertently, if the barbs 54 come into contact with the distal end face of the endoscope. In the embodiment as shown in FIG. 23 the barbs 54 are directly attached at the tube 2, if it is desired to have a stationary abutment, in contrast to the sleeve 53 which can be slided to adjust the desired length, with which the tube 2 protrudes.

Figure 24A:
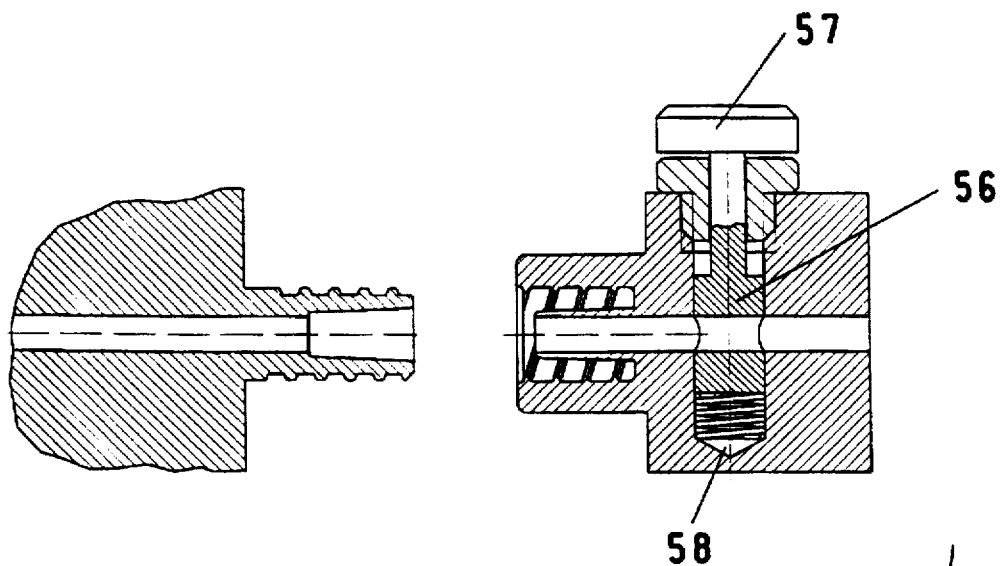
FIGS. 24a–b are schematic of a clamp used to hold tubes in position within the endoscope of FIG. 1.
Figure 24B:
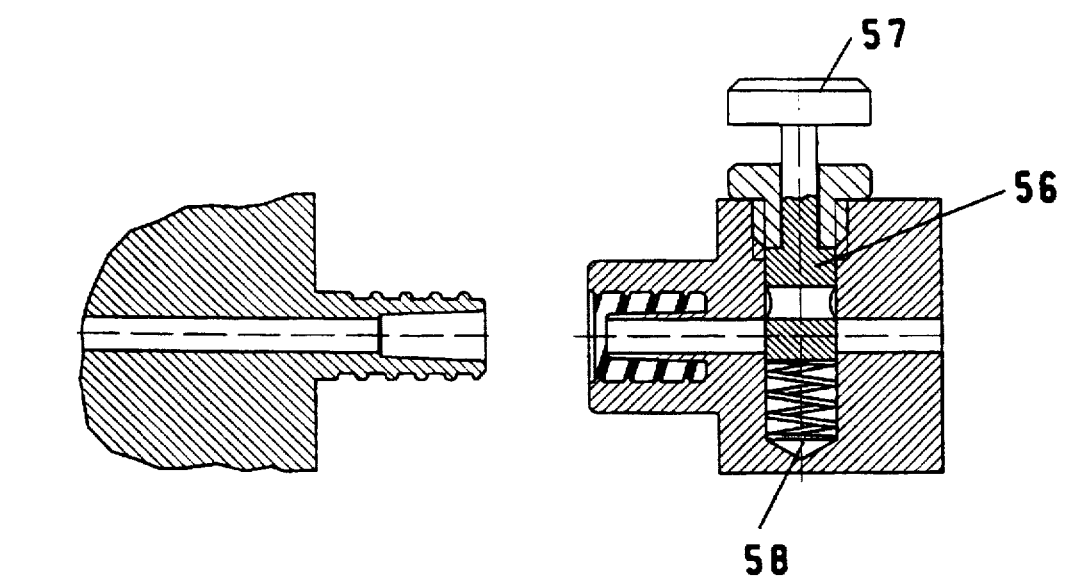

The surgeon can grip the proximal end region of the tube 2 which is shown in FIG. 1a, in order to move the tube in the direction into or out of the endoscope. In order to clamp the tube 2 in a desired position, in which the distal end of the tube 2 protrudes sufficiently out of the working channel 7, a clamping device 56 (FIG. 24) with a clamping key 57 is provided, which key 57 can be pressed down by the surgeon, if he wants to move the tube 2 in the forward or rearward direction. As soon as the desired length of the tube protrudes out of the distal end of the endoscope, the surgeon releases clamping key 57, so that the tube is fixed in the desired position by compressive force exerted by spring 58.

During use of the endoscope it is advisable to cause first a flow of the argon or other inert gas, in order to provide the cloud of the inert gas, before a discharge with a plasma jet is initiated, in order to provide a delay before the operative activation. In this manner it can be achieved, that a not desired ignition and discharge through the plasma jet is avoided, before a sufficient cloud of inert gas is available.

For argon plasma coagulation only endoscopes should be used whose electric insulation is absolutely reliable both exteriorly and in the instrument channel. Defective or inadequate insulation can cause patient burns and damage of the endoscope.

Only persons familiar with argon plasma coagulation (APC) characteristics, application and equipment should use APC in the gastrointestinal tract or in the trachea bronchial system. Before use a preoperative test of APC probe function should be performed before inserting it into the instrument channel of an endoscope. If the APC probe is inserted into the instrument channel of the endoscope, the distal end of the tube should emerge at least 10 mm from the distal end of the endoscope. This is the case, when the first black marking ring on the distal end of the probe is seen to emerge from the endoscope. The distal end of the APC probe should be no less than about 3 mm and no more than about 5 mm from tissue to ensure safe ignition and application of the argon plasma. The APC probe should never be activated while it is in contact with tissue. The distal tip of the APC probe should never be pressed against an organ wall before or during activation.

Excessive argon insufflation within the gastrointestinal tract (GIT) or the trachea bronchial system (TBS) should be avoided. During APC, distention of the organ being treated can cause discomfort to the patient. To avoid this, the argon flow rate should be set as low as possible. Repeated suction periods should be applied if using a single-channel endoscope. Continuous or interrupted suction through the second channel should be applied if using a double-channel therapeutic endoscope. A deflation tube (3-5 mm) should be inserted parallel to the endoscope. The patient's abdominal wall tension should always be monitored.

Coarse crusts of debris or tissue on the tip of the APC probe may inhibit argon flow through the probe. In such cases the APC probe should be pulled out and its tip cleaned with a wet swab. Before reinserting the APC probe into the endoscope, its function should be checked again.

A post operative cleaning, disinfection and sterilization of the APC probe should be performed by thoroughly rinsing the APC probe from proximal to distal as soon as possible after use with a suitable rinsing or disinfection solution. Also its exterior should be cleaned. The APC probes can be resterilized in autoclaves to 134° C. unless disposable probes are used, which are available in sterile wraps.

As mentioned above, a specific merit of the invention is to be seen in the fact, that a direct contact between metallic electrode and biologic tissue is avoided in a safe manner, so that the risk of a not controlled deep coagulation and a not intended cutting of the electrode into the tissue and therewith a perforation of this walled organs can be avoided.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An electrosurgical unit for achieving coagulation of tissue, comprising:
   an endoscope having:
      a proximal end and an opposing distal end, and
      a plurality of working channels extending between the two ends, each channel having a predetermined diameter and having an opening at each end;
   a flexible, hollow tube having a longitudinal axis disposed in one of the working channels of the endoscope, the tube having a diameter which is less than the diameter of the channel through which it is inserted, the tube including:
      a distal end and an opposing proximal end, each end of the tube having an opening, the tube having an inside and an outside,
      the tube positioned within the endoscope such that a portion of the tube including the opening at the distal end of the tube protrudes beyond the opening at the distal end of the endoscope and such that a gas stream exits from the opening at the distal end of the tube in order to establish an inert gas atmosphere between the distal end of the tube and the region of the tissue to be coagulated, and
      an electrode for ionizing the inert gas positioned inside the tube and offset from the opening at the distal end of the tube a predetermined minimum safety distance, such that the electrode can not come in contact with the tissue;
   a source of pressurized ionizable, inert gas connected to the opening at the proximal end of the tube and pressurized such that a stream of gas flows from the source, through the tube and exits through the opening at the distal end of the tube at a low flow rate of less than about 1 liter/minute;
   optical means positioned within a second working channel of the endoscope and protruding sufficiently from the opening at the distal end of the second channel of the endoscope to view the distal end of the tube and the tissue to be coagulated; and
   the portion of the tube protruding from the distal end of the endoscope positioned such that the longitudinal axis of the tube is arranged sidewardly of the area of tissue to be coagulated.

2. The electrosurgical unit for achieving coagulation of tissue of claim 1, wherein an opening at the distal end of the tube is positioned radially from the tube.

3. The electrosurgical unit for achieving coagulation of tissue of claim 1, wherein the opening at the distal end of the tube positioned longitudinally from the tube.

4. The electrosurgical unit for achieving coagulation of tissue of claim 1, wherein the gas comprising argon.

5. The electrosurgical unit for achieving coagulation of tissue of claim 1, wherein the electrode having an annular shape.

6. The electrosurgical unit for achieving coagulation of tissue of claim 1, wherein the electrode having a pin-shape.

7. The electrosurgical unit for achieving coagulation of tissue of claim 1, further comprising a manipulator operably connected at the distal end of the tube for controllably moving the opening at the distal end of the tube, the manipulator comprised of nonconductive material.

8. The electrosurgical unit for achieving coagulation of tissue of claim 7, wherein the manipulator comprising a rope, the rope attached to the distal end of the tube.

9. The electrosurgical unit for achieving coagulation of tissue of claim 8, wherein the manipulator comprising a rigid rod, the rod attached to the distal end of the tube.

10. The electrosurgical unit for achieving coagulation of tissue of claim 1, wherein the tube further comprising flexible bellows for adjusting the tube, the bellows positioned at substantially the distal end of the tube.

11. The electrosurgical unit for achieving coagulation of tissue during endoscopic surgery of claim 1, wherein an endpiece made out of a heat resistant material like ceramics is inserted into a distal end portion of the tube.

12. The electrosurgical unit for achieving coagulation of tissue during endoscopic surgery of claim 1, including means cooperating with the inert gas source for adjusting a first flow rate for standby operation and for a second flow rate during subsequent activation, in order to avoid that blood rests accumulate in the tube.

13. The electrosurgical unit for achieving coagulation of tissue during endoscopic surgery of claim 1, whereby the distal end portion of the tube protruding out of the distal end portion of the endoscope is provided with ring shaped markings permitting observation through said optical means how far the distal end of the tube protrudes out of the distal end of the working channel of the endoscope, into which the tube is inserted.

14. The electrosurgical unit for achieving coagulation of tissue during endoscopic surgery of claim 1, whereby a sleeve is fixed at an outer circumference of said tube, which sleeve is provided with barbs allowing to move the tube in the distal direction to protrude for a desired length out of the working channel if sufficient force is exerted by the surgeon, whilst the surgeon cannot retract the tube into the working channel as soon as the barbs come into engagement with the distal end of the endoscope.

15. The electrosurgical unit for achieving coagulation of tissue during endoscopic surgery of claim 1, whereby a clamping device with a clamping key is provided, or the endoscope which clamping key can be pressed down by the surgeon, if he wants to move the tube in a forward or rearward direction into a desired position, and that the surgeon can release the clamping key in a desired position of the protruding end portion of the tube, so that the tube is fixed in the desired position by compressive force exerted by spring means.

16. The electrosurgical unit for achieving coagulation of tissue during endoscopic surgery of claim 1, the distal end of the tube being provided with an end portion outwardly diverging to an exit opening of the tube.

17. An electrosurgical unit for achieving coagulation of tissue during endoscopic surgery, comprising:
   an endoscope having a proximal end and a distal end and having a plurality of working channels extending therebetween, each channel having an opening at each end, each channel having a predetermined diameter;
   a flexible, hollow tube having a longitudinal axis disposed in one of the working channels of the endoscope, the tube having a diameter which is less than the diameter of the channel through which it is inserted, the tube having:
      a distal end and an opposing, proximal end, each end of the tube having an opening, the tube having an inside and an outside, the opening at the distal end of the tube positioned radially from the tube, the tube positioned within the working channel such that a portion of the tube including the opening at the distal end protrudes beyond the opening at the distal end of the endoscope and the tube being aligned such that a gas stream exiting from the opening at the distal end of the tube is directed onto an area of tissue to be coagulated, and an electrode positioned inside the tube for ionizing the inert gas, the electrode being offset from the opening at the distal end of the tube a minimum safety distance, in such a manner that the electrode can not come into contact with the tissue;

a source of pressurized, ionizable inert gas connected to the opening at the proximal end of the tube and pressurized such that a stream of gas flows from the source, exits through the tube through the opening at the distal end of the tube; and the longitudinal axis of the portion of the tube that protrudes from the endoscope being positioned generally parallel to an area of tissue to be coagulated to achieve coagulation.

18. The electrosurgical unit for achieving coagulation of tissue during endoscopic surgery of claim 17, wherein the electrode having an annular shape.

19. The electrosurgical unit for achieving coagulation of tissue during endoscopic surgery of claim 17, wherein the electrode having a pin-shape.

20. The electrosurgical unit for achieving coagulation of tissue during endoscopic surgery of claim 17, further comprising a manipulator operably connected at the distal end of the tube for controllably moving the opening at the distal end of the tube, the manipulator comprised of nonconductive material.

21. The electrosurgical unit for achieving coagulation of tissue during endoscopic surgery of claim 20, wherein the manipulator comprising a rigid rod, the rod attached to the distal end of the tube.

22. The electrosurgical unit for achieving coagulation of tissue during endoscopic surgery of claim 17, wherein the tube further comprising flexible bellows for adjusting the tube, the bellows positioned at substantially the distal end of the tube.

23. The electrosurgical unit for achieving coagulation of tissue during endoscopic surgery of claim 17, wherein the gas comprising argon.

24. The electrosurgical unit for achieving coagulation of tissue during endoscopic surgery of claim 17, wherein an endpiece made out of a heat resistant material like ceramics is inserted into a distal end portion of the tube.

25. The electrosurgical unit for achieving coagulation of tissue during endoscopic surgery of claim 17, including means cooperating with the inert gas source for adjusting a first flow rate for standby operation and for a second flow rate during subsequent activation, in order to avoid that blood rests accumulate in the tube.

26. The electrosurgical unit for achieving coagulation of tissue during endoscopic surgery of claim 17, whereby the distal end portion of the tube protruding out of the distal end portion of the endoscope is provided with ring shaped markings permitting observation through optical means of how far the distal end of the tube protrudes out of the distal end of the working channel of the endoscope, into which the tube is inserted.

27. The electrosurgical unit for achieving coagulation of tissue during endoscopic surgery of claim 17, whereby a sleeve is fixed at an outer circumference of said tube, which sleeve is provided with barbs allowing the tube to move in the distal direction to protrude for a desired length out of the working channel if sufficient force is exerted by the surgeon, whilst the surgeon cannot retract the tube into the working channel as soon as the barbs come into engagement with the distal end of the endoscope.

28. The electrosurgical unit for achieving coagulation of tissue during endoscopic surgery of claim 17, whereby a clamping device with a clamping key is provided, on the endoscope which clamping key can be pressed down by the surgeon, if he wants to move the tube in a forward or rearward direction into a desired position, and that the surgeon can release the clamping key in a desired position, and that the surgeon can release the clamping key in a desired position of the protruding end portion of the tube, so that the tube is fixed in the desired position by compressive force exerted by spring means.

29. An electrosurgical unit for achieving coagulation of tissue during endoscopic surgery, comprising:

an endoscope having a proximal end and a distal end and having a plurality of working channels extending therebetween, each channel having an opening at each end, each channel having a predetermined diameter;

a flexible, hollow tube having a longitudinal axis disposed in one of the working channels of the endoscope, the tube having a diameter which is less than the diameter of the channel through which it is inserted, the tube having:

a distal end and an opposing, proximal end, each end of the tube having an opening, the tube having an inside and an outside, the tube positioned within the working channel such that a portion of the tube including the opening at the distal end protrudes beyond the opening at the distal end of the endoscope and the tube being aligned such that a gas stream exiting from the opening at the distal end of the tube is directed onto an area to be coagulated, and a source of pressurized, ionizable inert gas connected to the opening at the proximal end of the tube and pressurized such that a stream of gas flows from the source, exits through the tube through the opening at the distal end of the tube;

an electrode positioned inside the tube for ionizing the inert gas, the electrode being offset from the opening at the distal end of the tube a minimum safety distance, in such a manner that the electrode can not come into contact with the tissue, the longitudinal axis of the portion of the tube that protrudes from the endoscope being positioned generally parallel to an area of tissue to be coagulated to achieve coagulation, and means cooperating with the inert gas source for adjusting a first flow rate for standby operation and to the distal end opening of the tube.

30. The electrosurgical unit for achieving coagulation of tissue during endoscopic surgery of claim 29, wherein an end piece made out of a heat resistant material like ceramics is inserted into a distal end portion of the tube.

31. The electrosurgical unit for achieving coagulation of tissue during endoscopic surgery of claim 29, the distal end of the tube being provided with an end portion outwardly diverging to an exit opening of the tube.

32. The electrosurgical unit for achieving coagulation of tissue during endoscopic surgery of claim 29, whereby the distal end portion of the tube protruding out of the distal end portion of the endoscope is provided with ring shaped markings permitting observation through optical means how far the distal end of the tube protrudes out of the distal end of the working channel of the endoscope, into which the tube is inserted.

33. The electrosurgical unit for achieving coagulation of tissue during endoscopic surgery of claim 29, whereby a sleeve is fixed at an outer circumference of said tube, which sleeve is provided with barbs allowing to move the tube in the distal direction to protrude for a desired length out of the working channel if sufficient force is exerted by the surgeon, whilst the surgeon cannot retract the tube into the working channel as soon as the barbs come into engagement with the distal end of the endoscope.

34. The electrosurgical unit for achieving coagulation of tissue during endoscopic surgery of claim 29, whereby a clamping device with a clamping key is provided, on the endoscope which clamping key can be pressed down by the surgeon, if he wants to move the tube in a forward or rearward direction into a desired position, and that the surgeon can release the clamping key in a desired position of the protruding end portion of the tube, so that the tube is fixed in the desired position by compressive force exerted by spring means.

35. A method for coagulating tissue during endoscopic surgery comprising the following steps:

providing a surgical endoscope, the endoscope having a proximal end, an opposing distal end, an opening at each end, and a plurality of working channels extending between the openings at each end, each channel having a predetermined diameter, the endoscope having a flexible, hollow tube having a longitudinal axis inserted through one of the working channels of the endoscope, the tube having a diameter which is less than the diameter of the channel through which it is inserted, the tube having a distal end, an opposing proximal end connected to a source of ionizable, inert gas, an opening at each end, a channel extending between the two ends, an inside, an outside; and an electrode, arranged stationarily inside the tube and being offset from the opening at the distal end of the tube a predetermined minimum safety distance in such a manner that the electrode can not come into contact with the tissue; the tube positioned within the working channel of the endoscope such that the opening at the distal end Of the tube protrudes beyond the opening at the distal end of the endoscope, and can be observed through optical means provided at or near the distal end of said endoscope;

supplying the inert gas from the source of said gas through the tube to the distal end opening of said tube with such a low flow rate, that gas exiting through said distal end opening is a not directed, non laminar stream but forms an inert gas atmosphere between the distal end of the tube and the region of the tissue to be coagulated, while the distal end opening is maintained at a distance from the tissue to be coagulated in which situation the area of tissue to be coagulated is positioned sidewardly of the extended longitudinal axis of the said protruding end portion of said tube;

ionizing said inert gas atmosphere by activating a high frequency voltage source connected to the electrode by establishing an electric field in the inert gas atmosphere between the electrode and the sidewardly arranged area of tissue to be coagulated; and supplying an electric current by means of a plasma jet as a function of the direction of said electric field and the electric conductivity of the tissue surface to be coagulated, and coagulating an area of the tissue sidewardly of the extended longitudinal axis of the protruding end of the tube while the distal end opening of the tube is maintained in a substantially stationary position at a predetermined distance from the tissue to be coagulated, and while the ionized gas is being supplied through the distal end opening of the tube as a not directed, non laminar stream with a low flow rate.

36. The method as claimed in claim 35, whereby the coagulated area is many times larger than a cross sectional area of the distal end opening of the tube.

37. The method as claimed in claim 35, whereby a distal end portion of said tube is a tubular end piece made out of a heat resistant ceramic material.

38. The method as claimed in claim 35, whereby the stream of gas exits through said distal end opening with a flow rate of less than about one liter per minute.

39. The method as claimed in claim 38, whereby tissue in the gastrointestinal tract is coagulated.

40. The method as claimed in claim 37, whereby a stent is attached on tissue to be coagulated.

41. The method as claimed in claim 32, whereby tissue in the tracheobronchial system is coagulated.

42. The method as claimed in claim 38, whereby a gas stream with such a low flow rate is produced, that steam issuing from the heated tissue regions is displaced slowly but is not blown away abruptly.

43. The method as claimed in claim 35, whereby said not directed or nonlaminar gas stream is produced by using an outwardly diverging end portion at the distal end of said tube.

44. The method as claimed in claim 35, whereby delay means are used in order to avoid activation of said high frequency voltage source before a sufficient supply of said inert gas for forming said inert gas atmosphere has been performed.

45. The method as claimed in claim 44, whereby a first flow rate is adjusted for standby operation, whilst a second flow rate is adjusted during subsequent activation, in order to avoid that blood rests accumulate in the tube.

46. The method as claimed in claim 35, whereby the distal end portion of the tube protruding beyond the opening at the distal end of the endoscope is observed through said optical means provided at or near the distal end of said endoscope and is provided with ring-shaped markings and that it is observed how far tube protrudes out of the distal end of the working channel of the endoscope, and that a proximal portion of the tube extending out of the channel of the endoscope through which it is inserted is gripped by the surgeon to move the tube into a position of the distal end portion of the tube, so that the end portion of the tube protrudes along a sufficient length out of the distal end of the endoscope in order to avoid damage of the distal end of the of the endoscope during supplying said electric current by means of said plasma jet during operation.

47. The method as claimed in claim 46, whereby a sleeve is fixed at an outer circumference of said tube, which sleeve is provided with barbs allowing the tube to move in the distal direction to protrude for a desired length out of the working channel if sufficient force is exerted by the surgeon, whilst the surgeon cannot retract the tube into the working channel as soon as the bars come into engagement with the distal end of the endoscope.

48. The method as claimed in claim 35, whereby the surgeon can grip a proximal end region of the tube in order to move the tube in the direction into or out of the endoscope in order that the distal end portion of the tube protrudes with a sufficient length out of the end face of the endoscope, a clamping device with a clamping key can be actuated, which clamping key can be pressed down by the surgeon, if he wants to move the tube in the forward or rearward direction into a desired position, and that the surgeon releases the clamping key in a desired position of the protruding end portion of the tube, so that the tube is fixed in the desired position by compressive force exerted by spring means.

* * * * *

UNITED STATES PATENT AND TRADEMARK OFFICE
CERTIFICATE OF CORRECTION

PATENT NO. : 5,720,745
DATED : February 24, 1998
INVENTOR(S) : Guenther Farin, Karl Ernst Grund and Klaus Fischer It is certified that error appears in the above-indentified patent and that said Letters Patent is hereby corrected as shown below:

col. 3, line 57, after "schematic" please insert --views--.

col. 4, line 22, after "endoscope" delete "I" and insert therefor --1--.

col. 9, line 16, please replace the formula as follows:

$$V = f(P/R_1 + R_a).$$

Signed and Sealed this

Eleventh Day of August 1998

Attest:

BRUCE LEHMAN

Attesting Officer

Commissioner of Patents and Trademarks